(12) United States Patent
Maianti et al.

(10) Patent No.: US 8,585,969 B2
(45) Date of Patent: *Nov. 19, 2013

(54) DEVICE AND METHODS FOR PROCESSING BLOOD IN EXTRACORPOREAL CIRCULATION

(75) Inventors: Edgardo Costa Maianti, Mirandola (IT); Nicola Ghelli, San Pietro in Casale (IT); Ivo Panzani, Mirandola (IT)

(73) Assignee: Sorin Group Italia S.r.l., Mirandola (IT)

( * ) Notice: Subject to any disclaimer, the term of this patent is extended or adjusted under 35 U.S.C. 154(b) by 285 days.

This patent is subject to a terminal disclaimer.

(21) Appl. No.: 13/017,161

(22) Filed: Jan. 31, 2011

(65) Prior Publication Data

US 2011/0125074 A1 May 26, 2011

Related U.S. Application Data

(63) Continuation of application No. 12/331,082, filed on Dec. 9, 2008, now abandoned, which is a continuation of application No. 10/805,165, filed on Mar. 18, 2004, now Pat. No. 7,476,359.

(30) Foreign Application Priority Data

Apr. 1, 2003 (IT) .............................. MI20030148 U

(51) Int. Cl.
*A61M 1/00* (2006.01)
*A61M 37/00* (2006.01)

(52) U.S. Cl.
USPC ............. 422/45; 422/46; 604/6.09; 604/6.11; 604/6.13; 604/6.14

(58) Field of Classification Search
USPC .................. 604/4.01–6.16, 7–10; 422/44–48; 210/645

See application file for complete search history.

(56) References Cited

U.S. PATENT DOCUMENTS 2,319,730 A 5/1943 Garraway
2,659,368 A 11/1953 Gibbon, Jr.

(Continued)

FOREIGN PATENT DOCUMENTS

EP 0724889 A2 8/1996
EP 0987035 A2 3/2000

(Continued)

OTHER PUBLICATIONS

European Search Report issued in Application No. 03015535, mailed Oct. 24, 2003, 3 pages.

(Continued)

*Primary Examiner* — Philip R Wiest
(74) *Attorney, Agent, or Firm* — Faegre Baker Daniels LLP

(57) ABSTRACT

A device for treating blood in an extracorporeal blood circuit, the device including a centrifugal pump provided with a transparent enclosure that is connected, by means of an inlet duct, to the outlet of a venous reservoir, the venous reservoir having an inlet that is connected to receive blood from a patient. The transparent enclosure of the pump is connected monolithically to the base of a structure that comprises a heat exchanger and an oxygenator. The structure also supports monolithically, at the peripheral region, an arterial filter that receives the blood in output from the oxygenator and is provided with a connector for coupling to an arterial line for return of the blood to the patient.

10 Claims, 2 Drawing Sheets

(56) References Cited

U.S. PATENT DOCUMENTS

| | | | |
|---|---|---|---|
| 4,490,331 A | 12/1984 | Steg, Jr. | |
| 4,540,399 A | 9/1985 | Litzie et al. | |
| 4,610,656 A | 9/1986 | Mortensen | |
| 4,676,771 A | 6/1987 | Henke | |
| 4,698,207 A | 10/1987 | Bringham et al. | |
| 4,876,066 A | 10/1989 | Bringham et al. | |
| 5,039,482 A * | 8/1991 | Panzani et al. | 422/46 |
| 5,266,265 A | 11/1993 | Raible | |
| 5,270,005 A | 12/1993 | Raible | |
| 5,308,320 A | 5/1994 | Safar et al. | |
| 5,312,479 A | 5/1994 | Weinstein et al. | |
| H1324 H | 6/1994 | Dalke et al. | |
| 5,391,142 A | 2/1995 | Sites et al. | |
| 5,411,705 A | 5/1995 | Thor et al. | |
| 5,573,526 A | 11/1996 | Hess | |
| 5,582,794 A | 12/1996 | Hagiwara et al. | |
| 5,632,894 A | 5/1997 | White et al. | |
| 5,728,069 A | 3/1998 | Montevecchi et al. | |
| 5,762,869 A | 6/1998 | White et al. | |
| 5,770,149 A * | 6/1998 | Raible | 422/46 |
| 5,782,791 A | 7/1998 | Peterson et al. | |
| 5,817,278 A | 10/1998 | Fini et al. | |
| 5,823,987 A | 10/1998 | Elgas et al. | |
| 5,924,848 A | 7/1999 | Izraelev | |
| 5,958,338 A | 9/1999 | Lindsay et al. | |
| 6,059,111 A | 5/2000 | Davila et al. | |
| 6,162,017 A * | 12/2000 | Raible | 415/206 |
| 6,224,829 B1 | 5/2001 | Piplani et al. | |
| 6,306,346 B1 | 10/2001 | Lindsay | |
| 6,311,838 B1 | 11/2001 | Johnson et al. | |
| 6,428,747 B1 | 8/2002 | Dueri et al. | |
| 6,451,257 B1 | 9/2002 | Flamer | |
| 6,468,473 B1 | 10/2002 | Lindsay | |
| 6,503,450 B1 | 1/2003 | Afzal et al. | |
| 6,689,315 B2 | 2/2004 | Linker et al. | |
| 6,723,283 B2 | 4/2004 | Ghelli et al. | |
| 6,730,267 B2 * | 5/2004 | Stringer et al. | 422/45 |
| 6,773,426 B2 | 8/2004 | Tamari | |
| 6,852,280 B2 | 2/2005 | Vijay et al. | |
| 7,476,359 B2 * | 1/2009 | Maianti et al. | 422/46 |
| 2001/0010802 A1 | 8/2001 | Tamari | |
| 2002/0044889 A1 | 4/2002 | Aboul-Hosn et al. | |
| 2002/0049401 A1 | 4/2002 | Ghelli et al. | |
| 2002/0085952 A1 | 7/2002 | Ellingboe et al. | |
| 2003/0163078 A1 | 8/2003 | Fallen et al. | |
| 2004/0015042 A1 | 1/2004 | Vincent et al. | |
| 2004/0054316 A1 | 3/2004 | Maianti et al. | |
| 2004/0219060 A1 | 11/2004 | Maianti et al. | |
| 2004/0223873 A1 | 11/2004 | Maianti et al. | |
| 2009/0087342 A1 | 4/2009 | Maianti et al. | |

FOREIGN PATENT DOCUMENTS

| | | |
|---|---|---|
| EP | 1180374 A1 | 2/2002 |
| EP | 1197235 A1 | 4/2002 |
| EP | 1382358 A1 | 1/2004 |
| JP | 05095998 A | 4/1993 |
| JP | 08312536 A | 11/1996 |
| JP | 10057478 A | 3/1998 |
| JP | 2000176008 A | 6/2000 |
| JP | 2002536126 A | 10/2002 |

OTHER PUBLICATIONS

European Search Report issued in EP Application No. 04006206, mailed Aug. 3, 2004, 5 pages.

* cited by examiner

DEVICE AND METHODS FOR PROCESSING BLOOD IN EXTRACORPOREAL CIRCULATION

CROSS-REFERENCE TO RELATED APPLICATION

This application is a continuation of U.S. application Ser. No. 12/331,082, filed Dec. 9, 2008, entitled "Device and Methods for Processing Blood in Extracorporeal Circulation", which is a continuation of U.S. Pat. No. 7,476,359, filed Mar. 18, 2004, entitled "Device and Methods for Processing Blood in Extracorporeal Circulation"; which claims foreign priority of Italian Patent Application No. MI2003U000148, filed Apr. 1, 2003, all of which are hereby incorporated herein by reference in their entireties.

FIELD OF THE INVENTION

The invention relates to a method and device for processing blood in extracorporeal circulation. Reference is made to co-pending application U.S. Publn. No. 2004/0219060, filed on Mar. 18, 2004, and entitled "Device and Methods for Processing Blood in Extracorporeal Circulation" which is assigned to the assignee of the present invention and which is incorporated herein by reference in its entirety.

BACKGROUND OF THE INVENTION

During certain surgical procedures it is necessary to establish a circuit for extracorporeal circulation of the blood of the patient. Such circuits may comprise devices such as blood reservoirs which may include a venous reservoir, that is meant to collect the blood that leaves the patient, and a cardiotomy reservoir for containing the blood drawn by recovery from the operating field, a pump for conveying blood in the circuit, a heat exchanger in which the blood encounters a heat exchange surface that maintains blood temperature at a desired value, an oxygenation device that is meant to transfer oxygen to the blood, and finally a filter known as an arterial filter, that is connected in the arterial line and is meant to retain any air bubbles that are present in the blood before the blood is returned to the patient.

All these devices can be present in the extracorporeal circuit as separate elements or they can be integrated in various combinations such as disclosed in co-pending U.S. patent application Ser. No. 09/920,999 filed Aug. 2, 2001, (U.S. Pat. No. 6,723,283) which is assigned to the assignee of the present invention, and which is incorporated herein by reference in its entirety.

A need in this field exists, however, for a monolithic structure which integrates into a single package all of the various components necessary for use in an extracorporeal blood circuit used during heart bypass surgery or as an assist circuit during beating heart surgery.

SUMMARY OF THE INVENTION

An object of the present invention is to provide a device that ensures optimum conditions of removal of the air contained in the device during priming and use and which is configured to allow an operator of the device to maintain visual contact with critical portions of the device during use so that the operator can take corrective action when a problem situation is observed.

This object and other objects that will become better apparent hereinafter are achieved by a device for treating blood in extracorporeal circulation that comprises an integrated structure that includes a venous reservoir, a cardiotomy reservoir, a centrifugal blood pump, an oxygenator, a heat exchanger and an arterial blood filter, all of which are inter connected by means of various tubing lines and/or ducts. The integrated structure forms a complete system which includes all of the components required in an extracorporeal blood circuit used during heart bypass surgery or used to assist the heart during beating heart surgery. The integrated structure is configured to be shipped to a user as a completely assembled and interconnected system or alternatively, to more efficiently use packaging space some minimal assembly might be required by the user.

The integrated structure includes a centrifugal pump provided with a transparent enclosure that is connected, by means of an inlet duct, to the outlet of the venous reservoir. The inlet of the venous reservoir is connected to a venous line for conveying the blood from a patient. The transparent enclosure of the centrifugal pump is connected to the portion of the unitary structure that comprises the heat exchanger and oxygenator. The centrifugal pump may be a standard component which connects to the structure in a manner known in the art. Usually the centrifugal pump will be connected prior to packaging so that it is shipped and is received by the user as part of the monolithic structure although it could be shipped unconnected from the structure and connected by the user after receipt. That portion of the unitary structure comprising the oxygenator/heat exchanger has an inlet connected to receive blood from the centrifugal blood pump and also supports monolithically, at a peripheral region, the arterial filter. The arterial filter has an inlet connected to receive blood from an outlet of the oxygenator/heat exchanger. The arterial filter has an outlet connected to an arterial line for return of the blood to the patient.

In one embodiment the invention comprises an integrated device for oxygenating and filtering blood flowing through an extracorporeal blood circuit. The integrated device comprises a blood reservoir having an inlet for receiving venous blood and an outlet for supplying venous blood. The device includes a blood pump having an inlet connected to receive blood from the outlet of the blood reservoir and an outlet connected to a blood inlet of a heat exchanger. The heat exchanger has a blood outlet for supplying temperature controlled venous blood to the inlet of an oxygenator. The oxygenator has an outlet for supplying oxygenated blood to the inlet of an arterial blood filter. The arterial blood filter has an outlet adapted for connection to an arterial line for return of oxygenated blood to the patient. The integrated device includes a monolithic housing having a first portion for defining the blood reservoir, a second portion for defining the blood pump, a third portion for defining the heat exchanger, a fourth portion for defining the oxygenator and a fifth portion for defining the arterial blood filter.

The blood pump may comprise a centrifugal pump that is positioned within the monolithic housing such that an axis of the centrifugal pump is horizontal. The blood reservoir may comprise a combined venous reservoir and cardiotomy reservoir. Further, the monolithic housing of the integrated device may comprise connection means which allows removable connection of the first portion or the second portion of the housing.

In another embodiment the invention comprises a system for establishing an extracorporeal blood circuit. The system includes a blood reservoir, a blood pump, a heat exchanger, an oxygenator, an arterial blood filter and a housing for incorporating and interconnecting the blood reservoir, the blood pump, the heat exchanger, the oxygenator, and the arterial blood filter into a monolithic structure. The housing has an inlet for receiving venous blood from a patient and supplying the venous blood to the blood reservoir and an outlet for supplying oxygenated blood from the arterial blood filter to a patient.

The blood pump may comprise a centrifugal pump which is positioned within the housing such that an axis of the pump is horizontal. The blood reservoir may comprise a combined venous reservoir and cardiotomy reservoir. Further, the housing may comprise connection means for allowing removable connection of the blood reservoir or the centrifugal blood pump.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

Further characteristics and advantages will become better apparent from the description of two embodiments of the invention, illustrated by way of nonlimiting example in the accompanying drawings.

Figure 1:
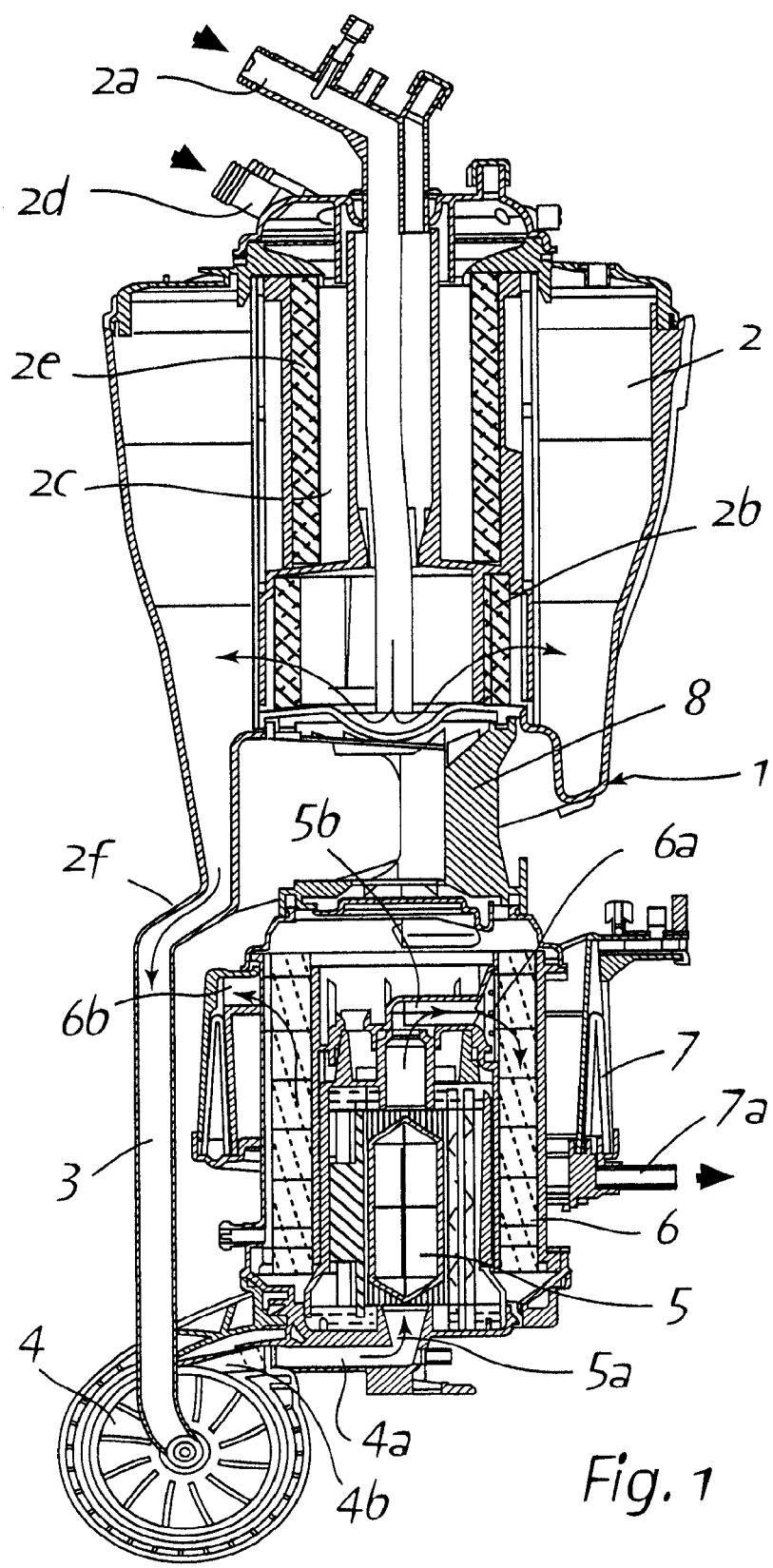
FIG. 1 is a longitudinal sectional view of the invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

BRIEF DESCRIPTION OF THE PREFERRED EMBODIMENTS

With reference to FIG. 1, the reference numeral 1 generally designates the device according to the invention, which comprises various components which have been integrated into a unitary or monolithic structure. These components are interconnected by various tubing lines or ducts to establish a blood flow path through the unitary structure according to the arrows shown in the figures and which will be described in detail, hereafter.

The unitary structure includes a venous reservoir 2, which is provided with an input connector 2a for connection to a venous line for receiving blood from the patient. Blood received from the patient through connector 2a passes through a filter 2b before it reaches venous reservoir 2. A cardiotomy reservoir 2c is contained within venous reservoir 2 and is connected receive blood recovered from the operating field through an inlet connector 2d. Blood received through inlet connector 2d passes through a filter 2e before it reaches venous reservoir 2.

An outlet connector 2f of venous reservoir 2 is connected at one end of duct 3. The other end of duct 3 is connected to an inlet of centrifugal pump 4. Centrifugal pump 4 has a transparent enclosure which defines an outlet connector 4b which is connected to delivery duct 4a, connected to provide blood from centrifugal pump 4 to an inlet connector 5a of heat exchanger 5. Heat exchanger 5 is provided with an outlet connector 5b that is configured to convey the blood to inlet 6a of oxygenator 6.

From the outlet 6b of the oxygenator 6, the blood reaches arterial filter 7, which is provided with an outlet connector 7a for connection to an arterial line for the return of the blood to the patient.

The transparent enclosure of the centrifugal pump 4 is connected monolithically to the end face of the structure that comprises the heat exchanger 5 and the oxygenator 6. Centrifugal pump 4 is oriented so that the pump axis is horizontal and outlet connector 4b is positioned at the top of the pump. This arrangement is beneficial for several reasons. First, it essentially ensures the complete removal of any air contained in the pump during its filling since any air bubbles in the device will rise because of their buoyancy and be expelled through the outlet connector at the top of the pump. Second, since the axis of the centrifugal pump is horizontal the entire rotor and pump chamber are visible to the operator through the transparent enclosure. This allows the operator to visually locate any air bubbles which may pass into or through the pump and to take appropriate corrective action in response thereto.

Furthermore, the ease with which the device may be set up and its operating convenience are both enhanced by the fact that the venous reservoir 2 is removably connected to a pedestal 8 that protrudes from that portion of the unitary structure that comprises the heat exchanger and the oxygenator by virtue of snap-acting means. This allows the venous reservoir/cardioplegia reservoir to be constructed as a first module of the system and the oxygenator/heat exchanger/arterial filter/pump to be constructed as a second module of the system. These two modules can be detached during shipment to conserve package space and assembled by the user by snap fitting the modules together during set up. Alternatively, they can be shipped completely assembled.

Figure 2:
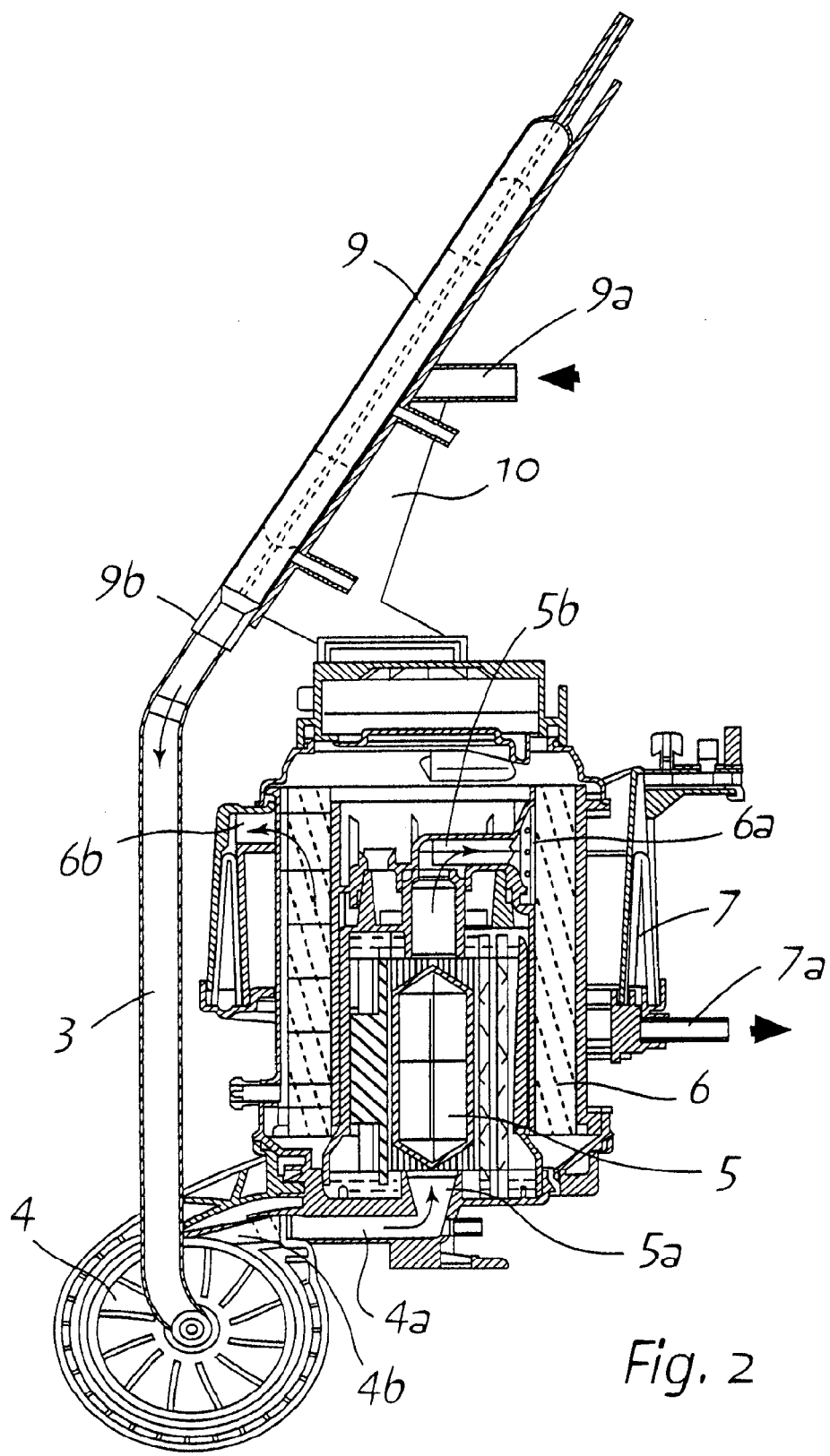
FIG. 2 is another longitudinal sectional view of the invention according to a different embodiment of the venous reservoir.

The embodiment shown in FIG. 2 differs from the one described above only in that rigid or hard shell venous reservoir 2 is replaced by a flexible bag 9. Bag 9 is connected to a support 10 that extends from the structure that comprises the heat exchanger and the oxygenator and is provided with an inlet connector 9a for connection to a venous blood inlet line and with an outlet connector 9b that is connected to the inlet of pump 4 through duct 3.

The device of the present invention may be used as a fast, efficient and convenient alterative to the use of various individual components in a traditional extracorporeal blood circuit. Since the structure of the device incorporates these various individual components into a preconnected monolithic structure it can be set up and ready for use very quickly. Further, the present invention is advantageous for use in beating heart surgery for several reasons. First, since part of the blood is diverted into an extracorporeal circuit the heart has less blood to pump and therefore beats less making it easier for the surgeon to work on the heart. Second, in cases where it is necessary to change to full bypass during the surgery the monolithic device of the present invention includes an oxygenator and other components which provide the capacity and function necessary to accommodate the change. The present invention also includes methods of using the device to process blood during heart bypass or beating heart surgery.

It should be understood that the embodiments disclosed herein represent presently preferred embodiments of the invention. Various modifications and additions may be made to these embodiments without departing from the spirit and scope of the invention.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An integrated device for oxygenating and filtering blood flowing through an extracorporeal blood circuit comprising:
    a blood reservoir having an inlet for receiving venous blood and an outlet for supplying venous blood;
    a blood pump having an inlet connected to receive blood from the outlet of the blood reservoir and an outlet arranged at a top of the blood pump such that any air bubbles in the blood received from the outlet of the blood reservoir will rise and be expelled through the outlet;
    a heat exchanger having a blood inlet connected to receive venous blood from the outlet of the pump and a blood outlet for supplying temperature controlled venous blood;
    an oxygenator having an inlet connected to receive venous blood from the outlet of the heat exchanger and an outlet for supplying oxygenated blood;
    an arterial blood filter having an inlet connected to receive oxygenated blood from the outlet of the oxygenator and an outlet for supplying filtered oxygenated blood; and
    a monolithic housing including a first portion for defining the blood reservoir, a second portion for defining the blood pump, a third portion for defining the heat exchanger, a fourth portion for defining the oxygenator and a fifth portion for defining the arterial blood filter, the second portion being configured such that the outlet of the blood pump is located at a top of the second portion of the monolithic housing;
        wherein the second portion of the housing is transparent to permit visualization of any air bubbles within the second portion of the housing.

2. The integrated device of claim 1 wherein the blood pump comprises a centrifugal pump.

3. The integrated device of claim 2 wherein the centrifugal pump has an axis and wherein the centrifugal pump is positioned within the monolithic housing such that the axis of the centrifugal pump is horizontal.

4. The integrated device of claim 1 wherein the blood reservoir comprises a venous reservoir and a cardiotomy reservoir.

5. The integrated device of claim 4 wherein the monolithic housing comprises connection means for allowing removable connection of the first portion.

6. A system for establishing an extracorporeal blood circuit comprising:
    a blood reservoir;
    a blood pump;
    a heat exchanger;
    an oxygenator;
    an arterial blood filter; and
    a housing for incorporating and interconnecting the blood reservoir, the blood pump, the heat exchanger, the oxygenator and the arterial blood filter into a monolithic structure, the housing having an inlet for supplying venous blood to the blood reservoir and an outlet for supplying oxygenated blood from the arterial blood filter, the housing further having a portion which defines the blood pump including a blood pump inlet and a blood pump outlet, the outlet of the blood pump being located at a top of the portion such that any air bubbles in the blood will rise and be expelled through the outlet;
    wherein the portion of the housing defining the blood pump is transparent to permit visualization of air bubbles within the portion.

7. The system of claim 6 wherein the blood pump comprises a centrifugal pump.

8. The system of claim 7 wherein the centrifugal pump has an axis and wherein the centrifugal pump is positioned within the housing such that the axis of the centrifugal pump is horizontal.

9. The system of claim 6 wherein the blood reservoir comprises a venous reservoir and a cardiotomy reservoir.

10. The integrated device of claim 9 wherein the housing comprises connection means for allowing removable connection of the blood reservoir.

* * * * *